United States Patent [19]
Sanghera et al.

[11] Patent Number: 5,849,174
[45] Date of Patent: Dec. 15, 1998

[54] ELECTRODES AND THEIR USE IN ANALYSIS

[75] Inventors: Gurdial Singh Sanghera, Newton, Mass.; Philip Nigel Bartlett, Alresford; Peter Robert Birkin, Southampton, both of United Kingdom

[73] Assignee: Medisense, Inc., Bedford, Mass.

[21] Appl. No.: 776,716

[22] PCT Filed: Aug. 1, 1995

[86] PCT No.: PCT/GB95/01818

§ 371 Date: Jun. 11, 1997

§ 102(e) Date: Jun. 11, 1997

[87] PCT Pub. No.: WO96/04398

PCT Pub. Date: Feb. 15, 1996

[30] Foreign Application Priority Data

Aug. 1, 1994 [GB] United Kingdom .................... 9415499

[51] Int. Cl.⁶ .................................................. G01N 27/26
[52] U.S. Cl. ....................... 205/775; 205/777.5; 205/778; 205/790.5; 205/791; 205/792; 205/793.5; 204/403; 204/415; 422/82.01; 422/82.02; 435/287.1; 435/289.1; 435/817
[58] Field of Search .................................. 205/775, 777.5, 205/778, 790.5, 791, 792, 793.5; 422/82.01, 82.02; 204/403, 415; 435/287.1, 289.1, 817

[56] References Cited

U.S. PATENT DOCUMENTS

| | | | |
|---|---|---|---|
| 5,202,261 | 4/1993 | Musho et al. | 435/288 |
| 5,250,439 | 10/1993 | Musho et al. | 435/25 |
| 5,352,574 | 10/1994 | Guiseppi-Elie | 204/403 |
| 5,403,451 | 4/1995 | Riviello et al. | 204/403 |

FOREIGN PATENT DOCUMENTS

WO 92/10584  6/1992  WIPO .
PCT/GB95/01818  8/1995  WIPO .

OTHER PUBLICATIONS

Bartlett et al., "Enzyme Switch Responsive to Glucose," *Anal. Chem.* 1118 (1993) No Month Available.

Bartlett, "Modified Electrode Surface in Amperometric Biosensors," *MBEC Biosensors special feature*, p. B10, (May 1990).

Chambers et al., The Development of Redox–Modified Electrodes as Charg–Accumulating Devices For Use In Higher Sensitivity Detection Systems, *J. Electroanal. Chem.* 250:417 (1988) No Month Available.

DiGleria et al., "Homogeneous Ferrocene–Mediated Amperometric Immunoassay," *Anal. Chem.* 1203 (1986) No Month Available.

Wehmeyer et al., "Competitive Heterogeneous–Enzyme Immunoassay for Digoxin with Electrochemical Detection," *Anal. Chem.* 135 (1986) No Month Available.

Wright et al., "Digoxin Homogeneous Enzyme Immunoassay Using High–Performance Liquid Chromatographic Column Switching with Amperometric Detection," *Anal. Chem.* 295 (1986) No Month Available.

*Primary Examiner*—Bruce F. Bell
*Attorney, Agent, or Firm*—Fish & Richardson P.C.

[57] ABSTRACT

A method for indicating the concentration of a substance in solution includes passing an alternating voltage between a first electrode structure having coated thereon a polymer and a second separate counter electrode in the solution. The polymer is in one of an oxidized and a reduced state, between which states its conductivity varies. Changes in the conductivity of the polymer coating are measured, the measurement being representative of the state of the polymer and thereby of the concentration of the substance in the solution. Electrodes for use in this method are also described.

19 Claims, 7 Drawing Sheets

ELECTRODES AND THEIR USE IN ANALYSIS

BACKGROUND OF THE INVENTION

1. Field of the Invention

This application is a 371 of PCT/GB95/01818 filed on Aug. 1, 1995.

This invention relates to electrochemistry and in particular to novel electrode structures and their use in analysis for the detection of enzymes or their substrates. The invention is of particular utility in sensors for biomedical applications.

2. Description of the Related Art

There is a continuing need for improved immunoassay techniques particularly for the detection of low levels of analytes in small samples.

In recent years, a number of electrochemical techniques have been developed in the hope of avoiding the generally conventional use of radioisotope labels for the detection of low levels of analytes. Direct amperometric measurements of NADH and of phenol has been reported by Wright et al *Anal. Chem.*, 58(1986) 2995 and by Wehmeyer et al *Anal. Chem.*, 58(1986) 135 employing enzyme-labelled antigens. The use of redox-labelled drug conjugates, specifically ferrocenyl-lidocaine for similar direct amperometric measurements has also been reported by Di Gleria et al *Anal. Chem.* 58(1986) 1203. These direct amperometric measurement techniques tend to suffer from a sensitivity limitation and in general the techniques are limited to low micromolar concentration ranges.

Chambers and Walton in *J. Electroanal. Chem.*, 250 (1988) 417–425 report use of a poly(vinylferrocene)-modified glassy carbon electrode used as a charge-accumulating device to a accumulate charge from a solution of glucose/glucose oxidase via the intermediary of a redox-labelled antigen, which is cycled repeatedly between the enzyme and the electrode. Chambers and Walton were able reproducibly to detect 1,1'-dimethylferrocene-3-ethan-1-ol-2-amine at nanomolar concentrations. Although Chambers and Walton identified 8-ferrocenyl-theophylline as their preferred redox-active mediator for further work, they found that it possessed a significant disadvantage in that it appeared to be bound unspecifically to anti-theophylline antibodies and so was not ideal for use in a competitive immunoassay.

A different approach has been adopted by Bartlett and Birkin, (*Anal. Chem.* 1993, 65, 1118–1119), namely the production of a DC bioelectrochemical transistor in the form of an enzyme switch. In this prior enzyme switch system, to provide a switch responsive to glucose, glucose oxidase was immobilized in a thin insulating film of poly(1,2-diaminobenzene) deposited on top of a poly(aniline) film deposited across a gap between two carbon electrodes. The change in conductivity of poly(aniline) between its oxidised and reduced states is measured by applying a small DC voltage from one carbon electrode to the other across the film and is used to measure the presence of redox mediator shuttling charge between the enzyme and polymer film. One drawback of this system is the need to form a polymer film which bridges the two electrodes, taking into account the minimum distance which can be tolerated between the electrodes.

SUMMARY OF THE INVENTION

The present invention has arisen from the work of the present inventors in seeking to improve upon the prior techniques.

As will be seen from the detailed description below, the methods and apparatus of the present invention draw upon the technology developed in connection with the prior enzyme switches, but apply this technology in a quite new way, namely in an alternating current system using a single polymer coated electrode.

In accordance with a first aspect of the present invention, there is provided a method for indicating the concentration of a substance in solution comprising passing an alternating voltage between a first electrode structure having coated thereon a polymer, the polymer being in one of an oxidised and a reduced state between which states its conductivity varies, and a second separate counter electrode in said solution; and measuring the change in conductivity of the polymer coating, such measurement being representative of the state of the polymer and thereby of the concentration of said substance in the solution.

For use in the above method the invention also provides an electrode structure forming a single electrode in a circuit comprising an electrode having coated thereon a polymer film the polymer being in one of an oxidised and a reduced state between which states its conductivity varies.

In a preferred embodiment of the invention, the method is used to provide an indication of the concentration of an enzyme substrate in solution. The enzyme is preferably immobilised in a film overlying the polymer coating and is involved in redox reactions with its substrate present in the solution. As the enzyme/substrate system undergoes redox reaction, charge is transferred to or from the polymer film bringing about a change in the oxidation state of the polymer. This change in oxidation state leads to a variation in the conductivity of the polymer. The rate at which this change occurs is dependent on the concentration of the substrate in solution so that by measuring the impedance of the system over time, the concentration of the substrate may be determined. Alternatively, a substrate may be immobilised on the polymer coating and the electrode is used to indicate the concentration of an enzyme in solution.

While in preferred embodiments, the electrode finds use in an enzyme system, we have also found that the method allows for direct measurement of substrates which undergo redox reactions. For example, NADH and L-ascorbic acid have been oxidised in the presence of a polymer film which undergoes reduction and thus changes from an insulating to a conducting state. This changes the conductivity of the film as outlined above to measure directly the concentration of a particular substance in solution. Alternatively, the system may be used to identify changes in the redox condition of the polymer film which are not a direct result of an enzyme/substrate system i.e. the background activity action, to provide a more accurate indication of the enzyme or substrate concentration.

Redox mediators may also be provided in the solution or immobilised on the support to transfer charge to or from the polymer film. As the substance or the substrate in the presence of the enzyme undergoes reduction or oxidation, the polymer support will also undergo oxidation or reduction either directly or through the use of mediators.

The method may also be carried out in the absence of the substance whose concentration is to be determined either with the enzyme electrode or base polymer film electrode to monitor background charges in the polymer conductivity which are not related to the concentration of the substance of interest.

The invention is described in detail with particular reference to the glucose/glucose oxidase system, employing poly(aniline) as the conductive polymer. The invention is not so limited but may be applied broadly to other enzyme/substrate systems and may also be used with other polymers with changing conductivity depending on their redox state.

The use of a single electrode associated with a polymer film allows for smaller electrodes to be produced having thinner coatings of polymer film. This has the advantage in that it is not necessary to form the film as a gap between two electrodes which may be difficult due to limitations in the minimum size gap that can be formed or tolerated without short-circuiting. Furthermore, the system is more sensitive when smaller quantities of polymer are used. Since the change in oxidation state of the polymer has a direct effect on conductivity, if less charge transfer is required to switch the polymer film from an insulating to a conducting state, the system becomes more sensitive to smaller quantities of substrate.

The electrode structure of the invention can be in the form of a micro electrode which enables commercial application of the technique as a bio-sensor where very small sample volume are involved, such as 10 $\mu$l. Analyte may be present in micromolar concentrations or less. The sensitivity of the system may allow concentrations in the femtomolar range to be detected, particularly where polymer films of thickness in the range 0.1 $\mu$m to 1 $\mu$m are applied to the electrode.

The invention has been described with reference to poly (aniline) which is insulating in its oxidised state and conducting in a reduced state. It may be readily returned to its oxidised state by holding the potential of the electrode at +0.4V vs. saturated calomel electrode (SCE) in a clean pH5 buffer solution.

BRIEF DESCRIPTION OF THE DRAWING

The invention is hereinafter described in more detail by way of example only with reference to the accompanying drawings in which.

DESCRIPTION OF THE PREFERRED EMBODIMENTS

The method of the present application involves forming a circuit comprising an electrode having coated thereon a polymer film and a counter electrode, an AC voltage being passed through the circuit to establish the impedance of the system between the electrodes. The conductance of the polymer film alters depending on the oxidation state of the polymer, which is in turn altered in response to oxidization or reduction reactions occurring to substrates in the solution in which the electrodes are placed.

Figure 1:
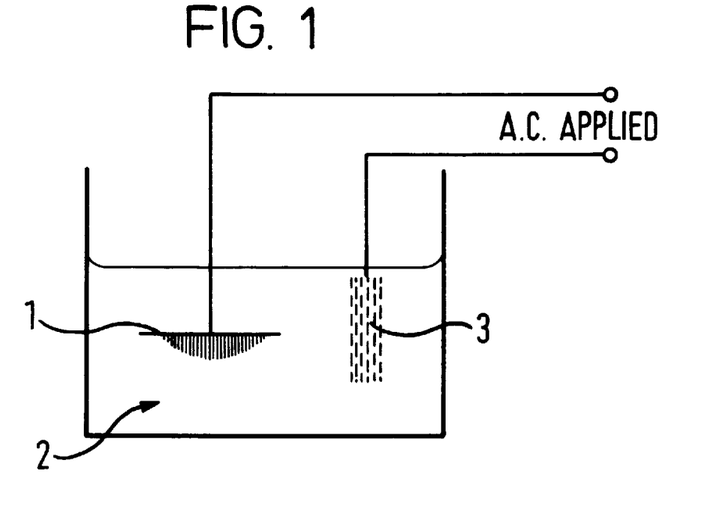
FIG. 1 is a drawing illustrating the experimental set up for use of an electrode structure in accordance with the present invention.
Figure 2:
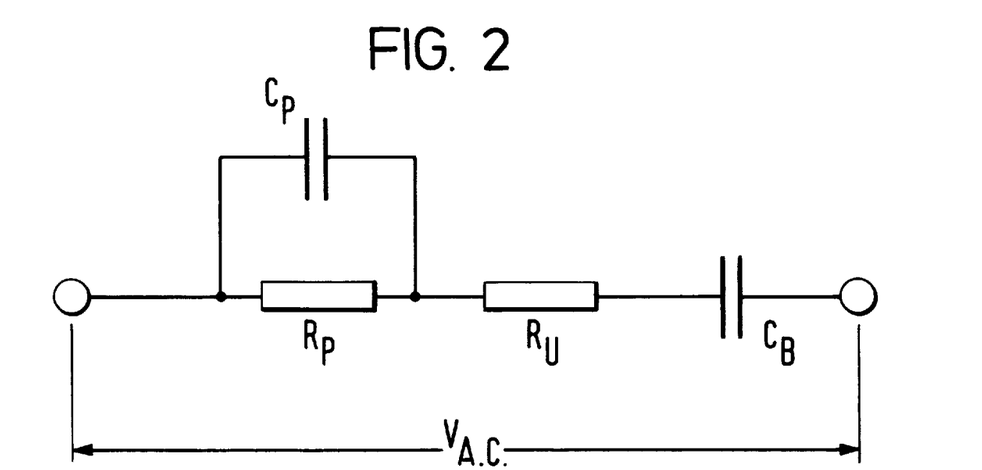
FIG. 2 is a circuit diagram of the system of FIG. 1.

Representative circuit diagrams are shown in FIGS. 1 and 2. The polymer coated electrode (1 of FIG. 1) is represented by the equivalent circuit of a resistance $R_p$ which ranges from 50 ohms to 100 kiloohms and a capacitance $C_p$ parallel. A blocking capacitor $C_b$ may be mounted in series with the electrode to prevent any unwanted DC signal affecting the oxidation state of the polymer. The resistance $R_u$ is uncompensated and represents the resistance of the solution (2) and of the counter electrode (3) which may suitably be formed of platinum gauze. An alternating voltage $V_{ac}$ is connected across the counter electrode and the blocking capacitor. The change in conductivity of the polymer film is readily detectable and the rate at which the film is switched from an insulating state to a conducting state (or vice versa) is dependent upon the concentration of the substrate in the solution which is undergoing redox reaction.

Figure 6:
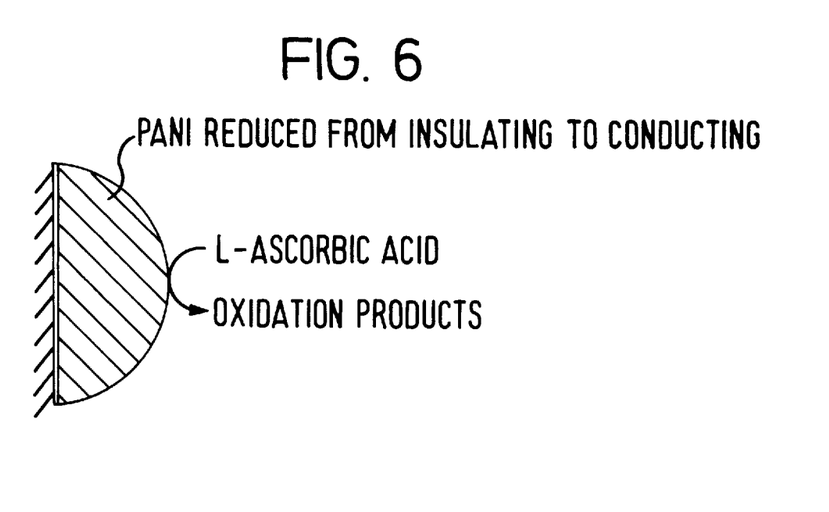
FIG. 6 is a schematic diagram of an alternative reaction scheme.

In its simplest form, a polymer film is formed over a carbon electrode. A suitable polymer is poly(aniline) which is insulating in its oxidised state and conducting in a reduced state. The change in the oxidation state of the poly(aniline) film is brought about by redox reactions occurring in the solution and/or at the polymer/solution interface. Mediators may be added to shuttle charge from the redox reactions occurring in the solution and the polymer film. An example of the reaction in its simplest form is shown at FIG. 6 where the oxidation of L-ascorbic acid leads to direct oxidation products while at the same time the poly(aniline) film is reduced from an insulating to conducting state. Similar results may be seen with NADH.

In an alternative aspect of the invention, the electrode is used in an enzyme system to measure the concentration of a substrate. In a preferred embodiment, the enzyme is immobilized in a thin insulating film on the polymer film. Such a system is the glucose/glucoseoxidase system exemplified by FIG. 5 where oxidation of glucose leads to reduction of the glucose oxidase enzyme. A mediator may be included such as tetrathiafulvalene or ferrocyanate $[Fe(CN)_6]^{3-}$.

While it is not essential for the enzyme to be bound in a separate layer over the polymer film, it is preferable. Binding the enzyme to the polymer electrode allows smaller quantities of enzyme to be used and aids ease of handling the device, and thus increases the reproducibility of results obtained with the device.

Figure 3:
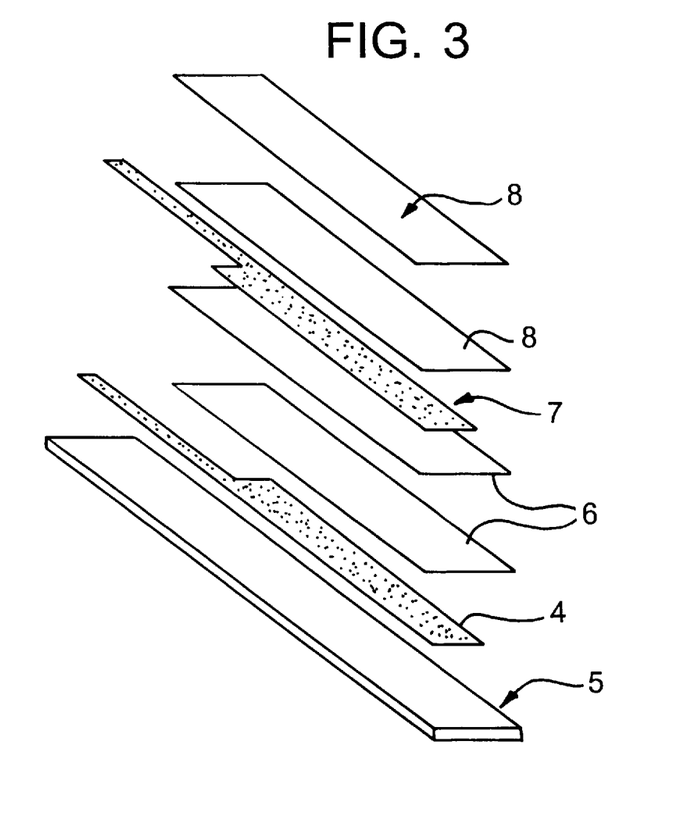
FIG. 3 is an exploded view of a carbon microband electrode used in the present application.

In a preferred aspect of the invention, the polymer electrode is formed as a number of carbon microband gap electrodes on which a polymer film is applied. These microband electrodes may be produced by screen printing onto a PVC card and are shown schematically in FIG. 3. Typically, each card may have a number carbon microband gap electrodes formed thereon which are subsequently separated. Firstly, a carbon electrode pattern (4) is printed onto a PVC card (5). Subsequently two layers of dielectric (6) are printed followed by a second carbon electrode layer (7) which lies directly over the first carbon electrode layer (4). Two more layers of dielectric (8) are applied to this second electrode layer (7). After each printing step, the PVC card is placed in an oven at 55° C. until the freshly applied layer has dried. Typically, this takes about 30 to 60 minutes. The carbon layers are determined to be dry when the resistance of the carbon track (measured with a Digital Volt Meter) reached a minimum constant value of typically of about one kiloohm. FIG. 3 shows an exploded view of a carbon microband single electrode having two carbon layers. A single carbon layer could also be used.

To expose the microband electrodes, the finished structures are sheared across the two carbon layers to expose the edges of the two carbon print layers. This is achieved by freezing the electrodes in liquid nitrogen and then fracturing them to avoid deformation and problems with shorting which can occur if the electrodes are cut mechanically to expose the carbon microband. The carbon microband electrodes are approximately 4.5 millimetres in length and 10 to 15 $\mu$m wide separated by a 20 $\mu$m gap.

A layer of poly(aniline) (PANI) is then grown on to the carbon microband electrode by holding the potential of the carbon electrode for 20 seconds at +0.9 V vs. SCE in a solution containing 200 $\mu$L of aniline and 5 cm$^3$ of NaHSO$_4$ acidified to a pH of approximately 0 with 0.5 cm$^3$ of concentrated H$_2$SO$_4$, suitably at 95–98% AR grade. Each of the above reagents may be obtained from Aldrich Chemical Co. Gillingham, Dorset. The typical total charge passed during this deposition was 3 mC, and corresponds to a film thickness in the region of 20 $\mu$m.

Figure 4:
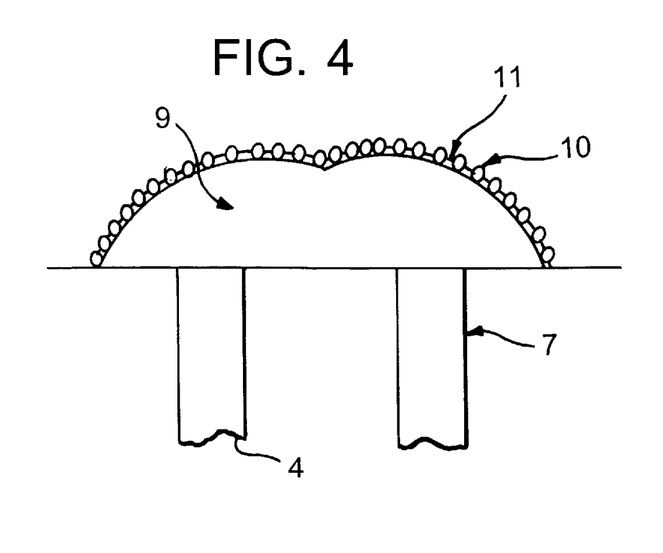
FIG. 4 is a greatly enlarged schematic representation of the cross section of an electrode of the present application.

FIG. 4 shows a schematic view of the electrode, having two carbon microband electrodes (4,7) having a poly (aniline) film (9) applied thereto. An enzyme (10) such as glucose oxidase is immobilised in an insulating film (11) applied to the surface of the poly(aniline) film (9). In the method of the invention, this electrode structure is used as a single electrode.

While the electrode described above has a 20 $\mu$m polymer film and a 20 $\mu$m gap, single electrodes for use in the present invention may be fabricated with significantly thinner coatings of polymer in the region of 0.1 to 1 $\mu$m enabling a wider range of polymer films to be applied and enhanced sensitivity.

Though it has been found that the use of poly(aniline) provides good results, this conductive polymer is pH dependent. The invention is not limited to the use of this specific polymer but can employ any other polymer which has an oxidized and a reduced state and is electrically conductive in one of these states.

Among the wide variety of electrically conductive polymers usable in practice of the present invention for appropriate systems are:

Poly(aniline) and derivatives thereof;
Poly(thiophene) and derivatives thereof;
Poly(pyrrole) and derivatives thereof; and
Poly(pyridine) and derivatives thereof.

Reference may be made to the specification of International Patent Application PCT/US88/02319 published under No: WO 89/01694 of Allied Signal, Inc which describes the manufacture and use of thermally stable forms of electrically conductive polyaniline. The polyaniline is rendered conductive by the use of a dopant solute which upon addition to the polyaniline ionizes the polymer with concomitant formation of an ionic dopant solute species. In general, suitable compounds for addition to the polymer have the formula:

where:
R is an organic radical;
$M^{+n}$ is a species having a positive charge equal to n, n being 1 to 4. In the preferred arrangement M is univalent and preferably hydrogen.

Similar such dopants may be incorporated in the poly (thiophene), poly(pyrrole), poly(indole) and poly(pyridine) systems. A wide variety of suitable monomers may be used for forming the polymers. The selection of individual monomers will have an effect on the film-forming properties as will the length of the polymer backbone, as will be well understood by polymer chemists and would be a matter of appropriate adjustment to provide a polymer of desired physical properties. By way of example, typical monomers are set out below for each of the abovenoted polymer systems:

Poly (aniline)

(m + n) is no greater than 5

Poly (pyrrole)

Poly (thiophene)

Poly (indole)

(m + n) is no greater than 4

Poly (pyridine)

(m + n) is no greater than 5

R, R$_1$, R$_2$, R$_3$ and R$_4$ are suitable organic radicals the selection of which will be well understood by polymer chemists. Most preferably, each of R, R$_1$, R$_2$, R$_3$ and R$_4$ will be lower alkyl (i.e., 1 to 4).

There is a substantial ease in detection by connecting the single electrode in a simple alternating current circuit. From the above, it is clear that by reference to a single electrode, a microband electrode structure may be used. By virtue of the presence of the counter electrode and the construction of the device, it is in effect a single electrode. No special reference electrode is required. Any appropriate counter electrode may be employed to complete the circuit since its resistance is in effect subsumed within the uncompensated resistance $R_u$ and what is being detected is the change in conductivity of the conductive polymer electrode.

An appropriate enzyme for the detection of glucose, an analyte of particular interest, is glucose oxidase. This enzyme is irreversibly damaged at a pH below 5 so that the enzyme is incompatible with the conditions in which the poly(aniline) film is grown. To produce an electrode structure in accordance with the present invention, the enzyme glucose oxidase is entrapped in an insulating poly(1,2-diaminobenzene) film which is electrochemically deposited on top of the poly(aniline) film. The poly(1,2-diaminobenzene) film is chosen because it can readily be electrochemically polymerized at a potential where poly(aniline) is conducting. It produces a highly active enzyme film. The practical steps performed in order to provide the enzyme coating consist of transferring the poly(aniline)-coated electrode to a solution of citric acid and $Na_2HPO_4$ solution at pH 5 containing 0.5 mol $dm^{-3}$ $Na_2SO_4$, 25 mmol $dm^{-3}$ 1,2-diaminobenzene, and 167 $\mu$mol glucose oxidase. The electrode is left in solution for six minutes to allow adsorption of the enzyme to the poly(aniline) surface. The poly(1,2-diaminobenzene) film was then deposited by holding the potential of the electrode at +0.4 V vs. SCE for 15 minutes.

Where $[Fe(CN)_6]^{3-}$ is used as a mediator, the electrode structure is placed in a stirred solution containing 3 $cm^3$ $[Fe(CN)_6]$ AT 50 mmolar in pH 5.0 buffer. The final electrode structure is stored at room temperature in pH 5.0 solution.

Figure 5:
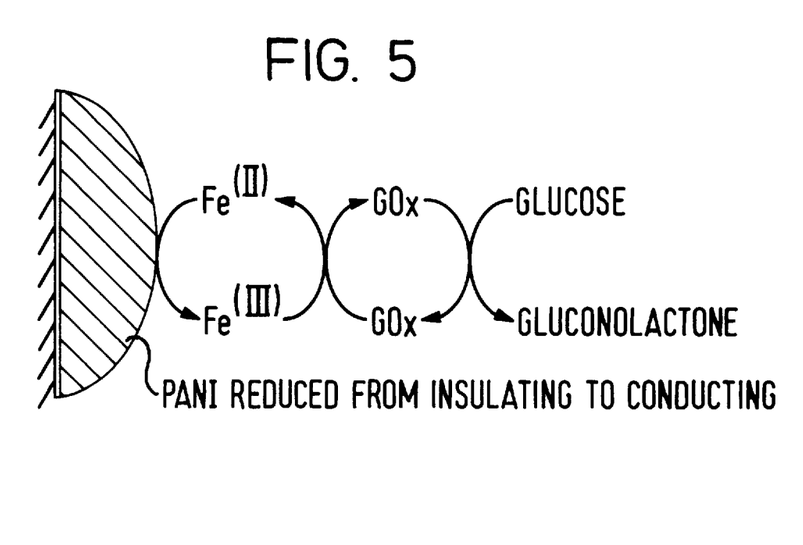
FIG. 5 is a schematic diagram of a reaction scheme of the present application.

Ferrocyanate ($[Fe(CN)_6]^{3-}$) acts as a redox mediator shuttling charge between the enzyme and conducting polymer, as shown schematically in FIG. 5. In its oxidized state at +0.5 V vs. SCE and at pH 5.0, poly(aniline) is insulating. On the addition of glucose, the film is reduced through the following reactions:

β-D-glucose+GOx(ox)→GOx(red)+gluconolactone

GOx(red)+2[Fe(CN)$_6$]$^{3-}$+→GOx(ox)+2[Fe(CN)$_6$]$^{2-}$

[Fe(CN)$_6$]$^{2-}$+PANI(ox)→[Fe(CN)$_6$]$^{3-}$++PANI(red)

where GOx(ox) and GOx(red) represent the oxidized and reduced forms of the enzyme, [Fe(CN)$_6$]$^{3-}$ and [Fe(CN)$_6$]$^{2-}$ are the oxidized and reduced forms of the mediator, and PANI (ox) and PANI(red) represent the oxidized, insulating state on the one hand and a reduced and conducting state on the other hand of the poly(aniline) film.

It may be desirable to place the electrode in solutions not containing glucose first to establish whether there are any background redox reactions occurring, affecting the conductivity of the polymer which are not directly related to the enzyme/substrate reactions.

Tetrathiafulvalene (TTF) may also be used as a mediator and is applied by placing the polymer coated electrode structure in a stirred solution containing 3 $cm^3$ pH 5.0 buffer, 50 $\mu$l of DM 50, 12 $\mu$l of Triton X100 and solid TTF for at least two hours. The final electrode structure is stored at room temperature in TTF containing solution. $TTF^+$ and TTF represent the oxidised and reduced forms of the mediator respectively.

Figure 7:
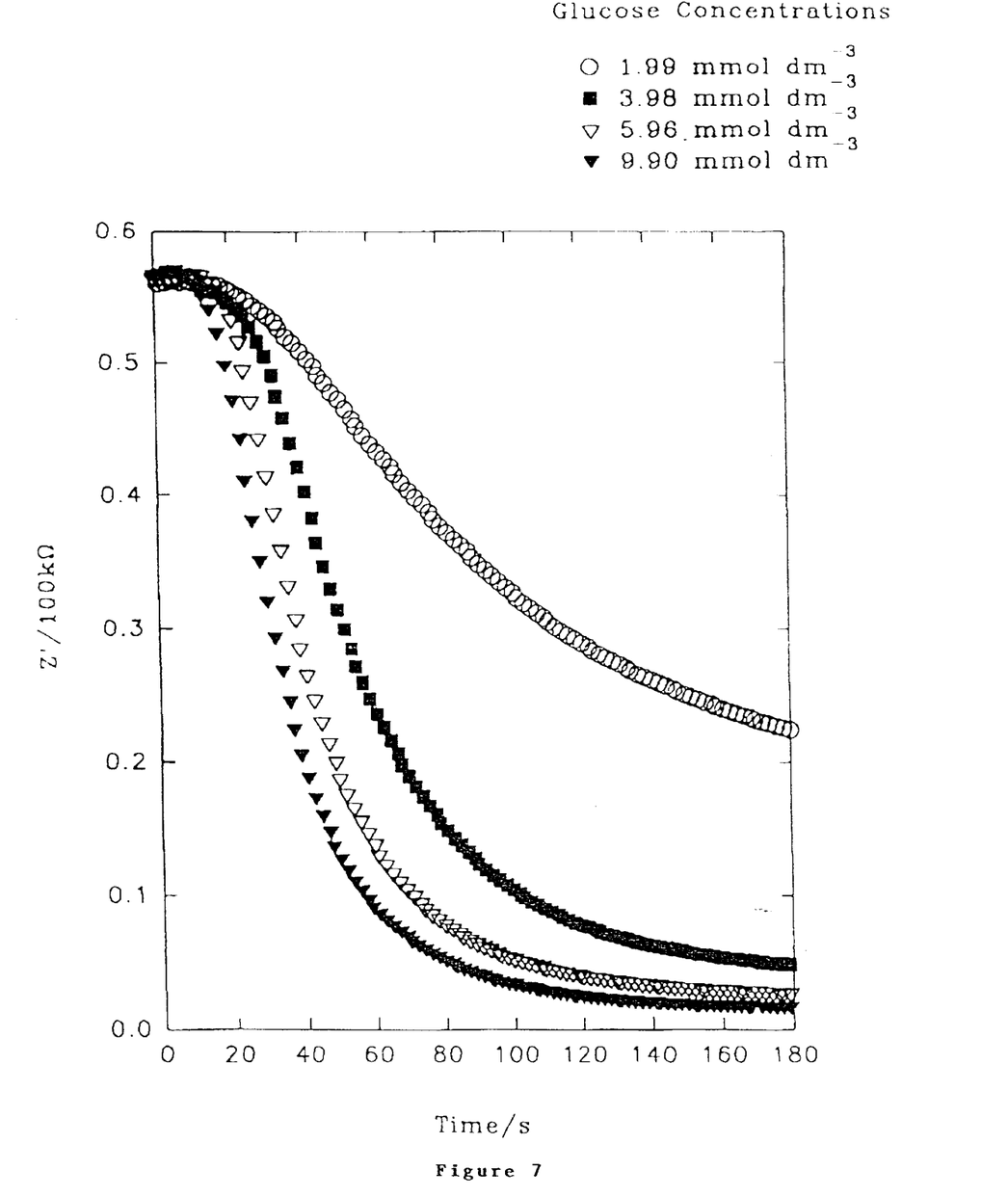
FIG. 7 shows measurements of impedance against time for one example of electrode structure in accordance with the present invention when exposed to different concentrations of glucose in solution.
Figure 8:
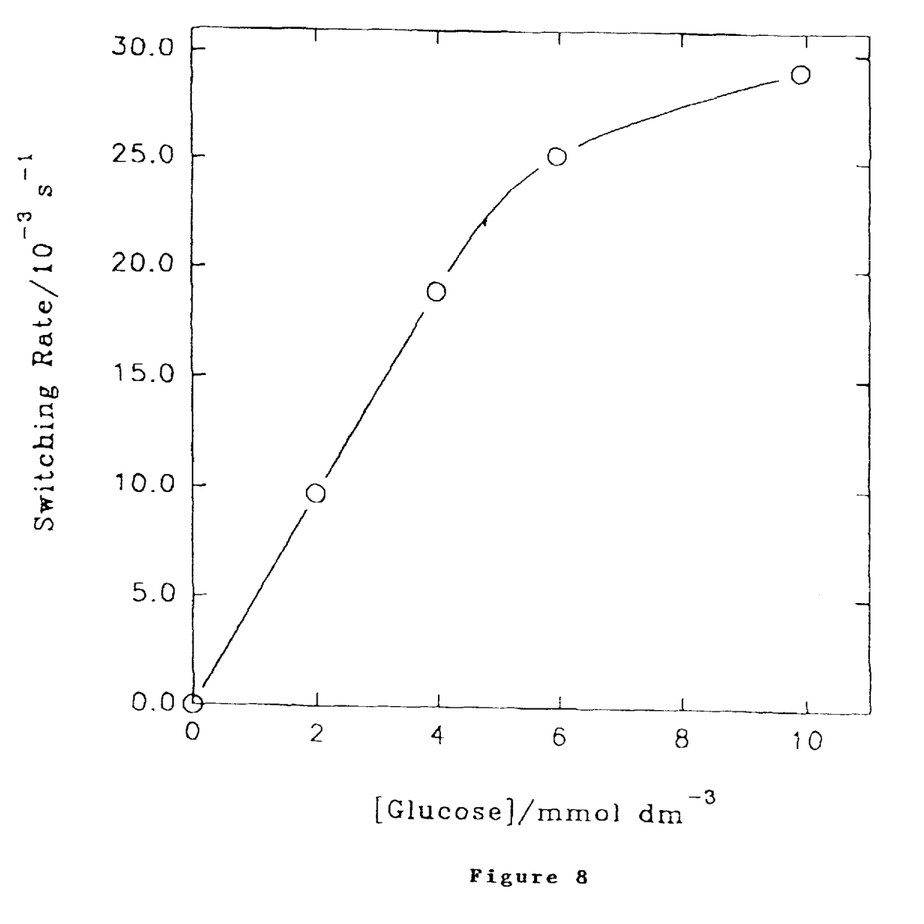
FIG. 8 shows how the glucose concentration is related to the switching rate (defined as the transient maximum gradient divided by the impedance change over the time period recorded) as derived from FIG. 7 for the electrode structure concerned.

The graphs illustrated in FIGS. 7 and 8 show the results obtained in measuring impedance of the poly(aniline) glucose oxidase electrode structure as against time with different concentrations of glucose in the solution. The switching rate of the device, defined as the transient maximum impedance gradient divided by the impedance change over the 180s of measurement, is plotted against glucose concentration in FIG. 8 from which it will be clear that there is a ready relationship between the switching rate and the glucose concentration. As a result, measurement of the switching rate for any unknown glucose concentration can readily identify the concentration.

Figure 9:
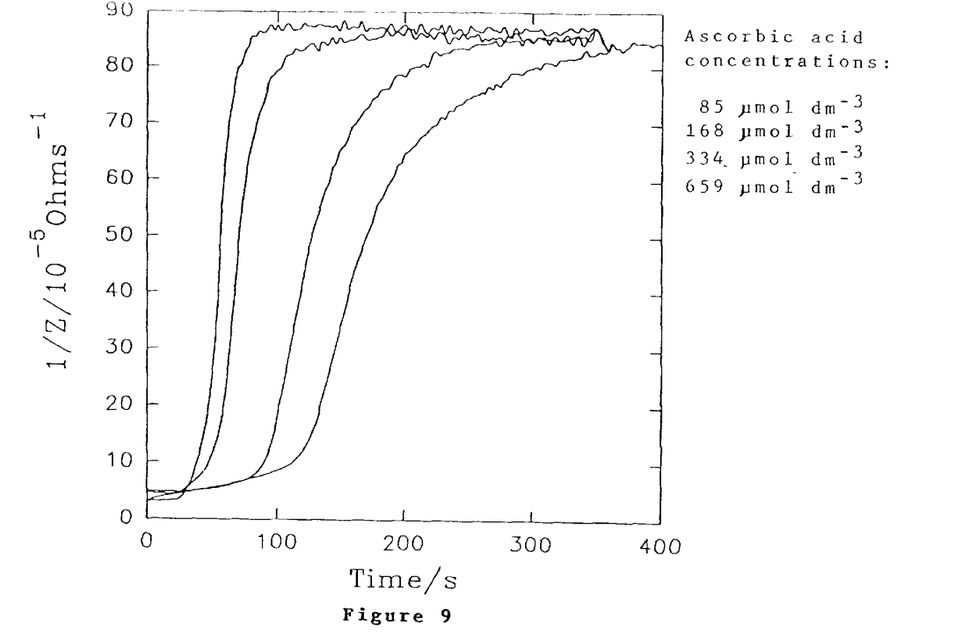
FIG. 9 shows measurement of impedance against time for an example of electrode structure in accordance with the present invention when exposed to difference concentrations of L-ascorbic acid in solution.
Figure 10:
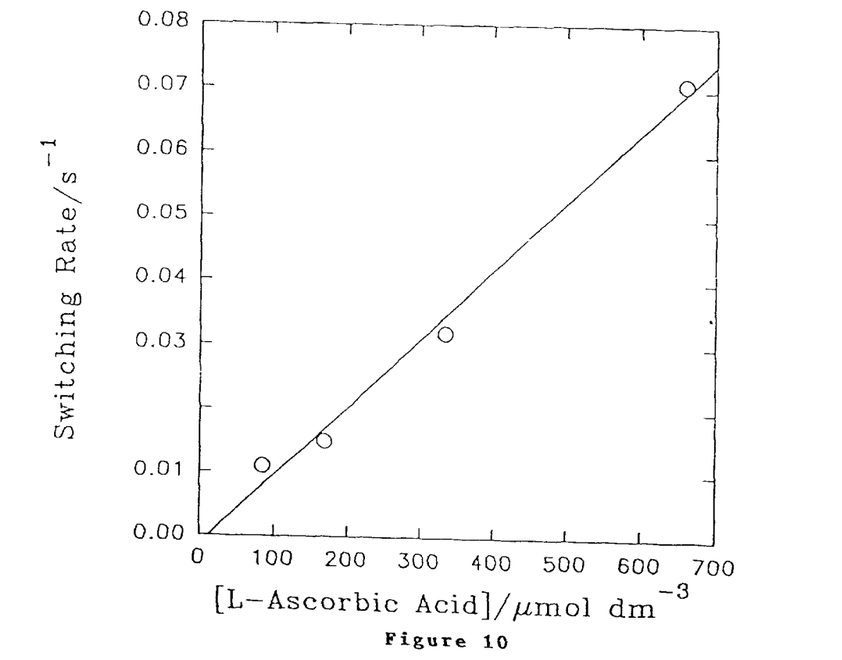
FIG. 10 shows how the ascorbic acid concentration is related to the switching rate as derived from FIG. 9 for the electrode structure concerned.

As an alternative to the enzymatic systems it is possible to employ bare poly(aniline) (PANI) to measure L-ascorbic acid. Again the same AC principle was employed, however, the fabrication of the device was much simpler requiring only the potentiostatic growth of poly(aniline) on an electrode. FIG. 9 shows the responses to L-ascorbic acid down to physiological ranges and FIG. 10 shows the corresponding switching rate.

In this system, as with the others, the response to L-ascorbic acid is concentration dependant. The system now is much simpler as demonstrated in FIG. 6.

This very simple system may be used to remove interference caused by L-ascorbic acid. The signal produced by ascorbic acid on a blank electrode could be used to adjust the sensor to the actual substrate concentration. In particular, L-ascorbic acid is a minor intereferant to the glucose system.

In a very similar way to L-ascorbic acid, NADH can be detected by the AC switch. Again only a bare poly(aniline) film is required and the oxidation of NADH on poly(aniline) shows the response of a single bare device to NADH. The system involves the reduction of poly(aniline) film from its insulating to conducting state.

Integration of the enzymatic response is performed during the process as each substrate molecule reacts and alters the redox potential and thus the impedance of the conducting polymer. The oxidation state change remains even if the structure is removed from the analyte solution. In effect, the polymer film records in a memory fashion any enzymatic reactions that have taken place. Accordingly, slow enzymatic reactions which would otherwise prove extremely difficult to accurately measure amperometrically can readily be detected and the concentration of the analyte estimated using the inherent integrating property of the conducting polymer in the single electrode device of the present invention.

The results presented above have been obtained using an electrode having a 20 $\mu$m polymer film and have shown the effectiveness of measurements in an AC circuit. Using the polymer coated electrode as a single electrode, much smaller electrodes could be used requiring only a very thin film of polymer in the range of 0.1 to 1 $\mu$m. In view of the mechanism by which the oxidation changes in the polymer lead to conductivity charges which can be correlated to substance concentration, such thinner films greatly enhance the sensitivity of the system to lower concentrations, down to femtomolar ranges. Furthermore, the presence of a thinner coating which does not need to bridge a gap between electrodes increases the flexibility of the system and extends the range of polymers which can be used.

Miniaturization of the device is possible down to microelectrode dimensions since a large electrode area is not required even for detection of low level analyte concentrations.

Repeated electrochemical oxidation of the polymer after each measurement can be used to reset the polymer to its original oxidation state. This means that a single electrode structure may be used to make a series of measurements on the same solution. This increases accuracy of use since the estimate of concentration can be given as the average of numerous separate responses using the same device.

The use of a specific redox mediator such as ferrocene or TTF is not essential in the system. The enzyme itself may be modified by incorporating a chemically modified covalent redox group in the enzyme, thereby removing the need for the homogenous mediator.

The invention is applicable to other enzyme systems such as horseradish peroxidase and NADH dependent enzymes.

While the invention has been described by reference to a single polymer coated electrode, devices could be constructed where a plurality of electrodes are formed on a single base card, each being used independently of the others to complete a circuit. Different polymer coatings or enzyme systems may be applied to the different electrodes so that sequential AC interrogation of each electrode using the same counter electrode will provide information for a number of different substances or substrates in the solution. Thus, a single device may be provide for a number of substances using the same basic circuitry for each test.

Figure 11:
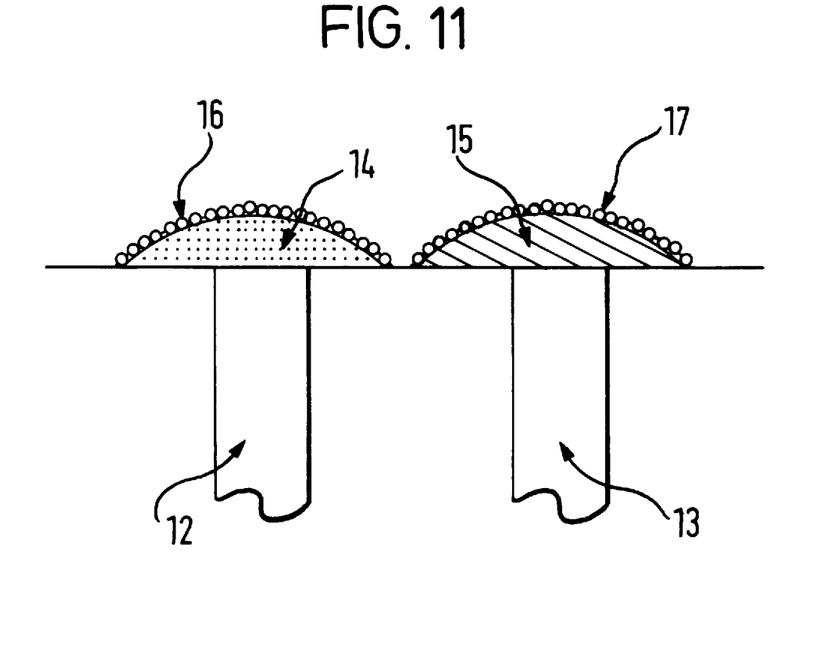
FIG. 11 is a schematic representation of the cross section of an alternative electrode of the present application.

FIG. 11 shows an example of such a device wherein two carbon electrodes (12, 13) have coated therein a polymer film (14, 15) which may be the same or different. A separate enzyme system (16, 17) may be applied to each polymer film such as horse radish peroxidase in any insulating film and glucose oxidase in an insulating film. Each electrode (12, 13) is connected in the AC circuit separately to obtain a reading for the electrode/polymer/enzyme system employed. Additional electrodes could be provided with the same or different polymer films and with or without an enzyme system.

We claim:

1. A method for indicating the concentration of a substance in solution comprising passing an alternating voltage between a first electrode structure having coated thereon a polymer, the polymer being in one of an oxidised and a reduced state between which states its conductivity varies, and a second separate counter electrode in said solution; and measuring the change in conductivity of the polymer coating resulting from a chance in the state of the polymer due to a transfer of charge between the substance and the polymer, such measurement being representative of the state of the polymer and thereby of the concentration of said substance in the solution.

2. A method according to claim 1 wherein a first measurement is made in the absence of the substance in solution to provide a background reading of any interfering substances in said solution.

3. A method according to claim 1 or 2 wherein a substrate for an enzyme is immobilised on the polymer coating and the method is for indicating the concentration of the enzyme in the solution.

4. A method according to claim 1 wherein an enzyme is immobilised on the polymer coating, and the method is for indicating the concentration of a substrate for said enzyme in the solution.

5. A method according to claim 4 wherein said first electrode comprises a mediator associated with the polymer or enzyme coating, for transfer of charge between the substrate and the polymer.

6. A method according to claim 4 or claim 5 wherein a first measurement is made in the absence of said enzyme to provide a background reading of any interfering substances in said solution.

7. A method according to claim 1 wherein the polymer comprises poly(aniline).

8. A method according to claim 1 wherein the polymer film has a thickness in the range of 0.1 to 1 $\mu$m.

9. A method according to claim 1 wherein the first electrode structure comprises a plurality of electrodes each using a discrete polymer coating thereon, and an alternating voltage is passed through each electrode separately to measure the state of the conductivity of each, polymer coating and thereby the concentration of a plurality of substances in solution.

10. An electrode structure forming a single electrode in a circuit comprising an elongate electrode having an exposed face over which a polymer is coated, the polymer being in one of an oxidised and a reduced state between which states its conductivity varies.

11. An electrode structure according to claim 10 wherein the polymer film is covered by a composition in which an enzyme is immobilised.

12. An electrode according to claim 10 wherein said electrode comprises a carbon microband electrode having one or more carbon electrodes inter-layered with insulating dielectric layers printed on a substrate, each carbon electrode having an exposed end of carbon, the polymer being coated on the exposed ends of carbon of said microband electrode.

13. An electrode according to claim 10 wherein said polymer film has a thickness in the range of 0.1 to 1 $\mu$m.

14. An electrode structure according to claim 10 and comprising a plurality of electrodes each having coated thereon a discrete polymer film.

15. An electrode structure according to claim 14 wherein an enzyme is overcoated onto one of the discrete polymer films.

16. An electrode structure forming a single electrode in a circuit comprising a carbon microband electrode having one or more carbon electrodes inter-layered with insulating dielectric layers printed on a substrate, each carbon electrode having an exposed end of carbon over which a polymer is coated, the polymer being in one of an oxidised and a reduced state between which states its conductivity varies.

17. An electrode according to claim 16 wherein said polymer film has a thickness in the range of 0.1 to 1 $\mu$m.

18. An electrode structure according to claim 16 and comprising a plurality of electrodes each having coated thereon a discrete polymer film.

19. An electrode structure according to claim 16 wherein an enzyme is overcoated onto one of the discrete polymer films.

* * * * *